(12) United States Patent
Onobori et al.

(10) Patent No.: US 10,258,300 B2
(45) Date of Patent: Apr. 16, 2019

(54) RADIATION IRRADIATION DEVICE

(71) Applicant: FUJIFILM Corporation, Tokyo (JP)

(72) Inventors: Noriyuki Onobori, Kanagawa (JP);
Ryosuke Ogura, Kanagawa (JP);
Takeyasu Kobayashi, Kanagawa (JP);
Yusuke Kitagawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/963,983

(22) Filed: Apr. 26, 2018

(65) Prior Publication Data

US 2018/0242934 A1 Aug. 30, 2018

Related U.S. Application Data

(63) Continuation of application No. PCT/JP2016/083458, filed on Nov. 11, 2016.

(30) Foreign Application Priority Data

Nov. 26, 2015 (JP) .................................. 2015-230364
Apr. 12, 2016 (JP) .................................. 2016-079511

(51) Int. Cl.
*A61B 6/00* (2006.01)
*A61B 90/50* (2016.01)

(52) U.S. Cl.
CPC .............. *A61B 6/4405* (2013.01); *A61B 6/00* (2013.01); *A61B 6/40* (2013.01); *A61B 6/462* (2013.01); *A61B 6/563* (2013.01); *A61B 90/50* (2016.02)

(58) Field of Classification Search
CPC ......... A61B 6/4405; A61B 6/46; A61B 6/461; A61B 6/462
See application file for complete search history.

(56) References Cited

U.S. PATENT DOCUMENTS 4,625,731 A * 12/1986 Quedens .............. A61B 6/447
348/825
5,901,200 A * 5/1999 Krause ................ A61B 6/4405
378/197

(Continued)

FOREIGN PATENT DOCUMENTS

| CN | 103169487 | 6/2013 |
| CN | 104411244 | 3/2015 |

(Continued)

OTHER PUBLICATIONS

"International Search Report (Form PCT/ISA/210) of PCT/JP2016/083458," dated Jan. 24, 2017, with English translation thereof, pp. 1-5.

(Continued)

*Primary Examiner* — Thomas R Artman
(74) *Attorney, Agent, or Firm* — JCIPRNET

(57) ABSTRACT

Provided is a radiation irradiation device enabling a user to change the position of a monitor to a desired position as needed and smoothly perform imaging of a radiographic image. The radiation irradiation device includes a radiation generation unit that generates radiation; a second support part having one end to which the radiation generation unit is attached; a first support part having one end to which the second support part is connected and the other end connected to a body part; the body part; a leg part that is provided on a bottom surface of the body part and is capable of traveling on a device placement surface; and a monitor provided on a surface that faces the bottom surface of the body part, via a connecting member. The monitor is detachably installed at a plurality of positions on the surface that faces the bottom surface of the body part.

21 Claims, 8 Drawing Sheets

(56) References Cited

U.S. PATENT DOCUMENTS

| | | | |
|---|---|---|---|
| 7,611,282 B2* | 11/2009 | Koren | A61B 6/4233 |
| | | | 378/198 |
| 8,690,425 B2* | 4/2014 | Kopcienski | A61B 6/4405 |
| | | | 378/102 |
| 9,295,438 B2* | 3/2016 | Omura | A61B 6/4405 |
| 9,398,675 B2* | 7/2016 | Eaves | A61B 6/4233 |
| 9,402,586 B2 | 8/2016 | Tsujii | |
| 9,413,961 B2* | 8/2016 | Welsh | A61B 6/4405 |
| 9,693,746 B2 | 7/2017 | Ancar | |
| 9,700,278 B2* | 7/2017 | Tezuka | A61B 6/563 |
| 9,808,218 B2* | 11/2017 | Tezuka | A61B 6/563 |
| 10,136,866 B2* | 11/2018 | Onobori | A61B 6/00 |
| 2009/0034688 A1* | 2/2009 | Koren | A61B 6/4233 |
| | | | 378/198 |
| 2014/0233703 A1* | 8/2014 | Omura | A61B 6/4405 |
| | | | 378/98 |
| 2015/0049862 A1 | 2/2015 | Ancar | |
| 2015/0078529 A1* | 3/2015 | Tsubota | H04W 76/10 |
| | | | 378/98 |
| 2015/0350545 A1* | 12/2015 | Welsh | A61B 6/4405 |
| | | | 348/77 |
| 2016/0022242 A1* | 1/2016 | Tezuka | A61B 6/563 |
| | | | 250/393 |
| 2017/0265835 A1* | 9/2017 | Tezuka | A61B 6/563 |
| 2017/0374728 A1* | 12/2017 | Kuranisi | A61B 6/4405 |
| 2018/0000443 A1* | 1/2018 | Matsuura | A61B 6/4405 |
| 2018/0014396 A1* | 1/2018 | Imamura | H05G 1/265 |
| 2018/0035524 A1* | 2/2018 | Matsuura | A61B 6/56 |
| 2018/0192979 A1* | 7/2018 | Tsuji | A61B 6/10 |
| 2018/0235558 A1* | 8/2018 | Onobori | A61B 6/00 |
| 2018/0242933 A1* | 8/2018 | Sanbuichi | A61B 6/00 |

FOREIGN PATENT DOCUMENTS

| | | |
|---|---|---|
| JP | 2006055201 | 3/2006 |
| JP | 2007000535 | 1/2007 |
| JP | 2009201832 | 9/2009 |
| JP | 2009201936 | 9/2009 |
| JP | 2010240339 | 10/2010 |
| JP | 2014155620 | 8/2014 |
| JP | 2014204783 | 10/2014 |
| JP | 2015062446 | 4/2015 |
| JP | 2015083113 | 4/2015 |
| JP | 2015514549 | 5/2015 |

OTHER PUBLICATIONS

"Written Opinion of the International Searching Authority (Form PCT/ISA/237) of PCT/JP2016/083458," dated Jan. 24, 2017, with English translation thereof, pp. 1-6.

"Notification of Reasons for Refusal of Japanese Counterpart Application," dated Sep. 6, 2016, with English translation thereof, pp. 1-7.

"Office Action of China Counterpart Application," with partial English translation thereof, dated Oct. 17, 2018, p. 1-p. 12.

* cited by examiner

RADIATION IRRADIATION DEVICE

CROSS-REFERENCE TO RELATED APPLICATIONS

This application is a Continuation of PCT International Application No. PCT/JP2016/083458 filed on Nov. 11, 2016, which claims priority under 35 U.S.C § 119(a) to Japanese Patent Application No. 2015-230364 filed on Nov. 26, 2015 and Japanese Patent Application No. 2016-079511 filed on Apr. 12, 2016. Each of the above application(s) is hereby expressly incorporated by reference, in its entirety, into the present application.

BACKGROUND OF THE INVENTION

1. Field of the Invention

The present invention relates to a radiation irradiation device having an arm part provided with a radiation source.

2. Description of the Related Art

In the related art, portable radiation irradiation devices used in a case where a patient's radiographic image is captured in operating rooms, examination rooms, or patients rooms have been suggested variously (refer to JP2014-204783A, JP2015-83113A, and JP2006-55201A).

The portable radiation irradiation devices basically include a leg part enabled to travel by wheels, a body part that houses a control unit including a battery for driving a radiation source, an electric circuit related to the driving of the radiation source, and the like and is held on the leg part, and an arm part connected to the body part, and are configured by attaching the radiation source to a tip of the arm part.

In a case where such radiation irradiation devices are used, a radiation irradiation device is first moved to the vicinity of a patient's bed. Next, the radiation source is moved to a desired position, and a radiation detector is moved to a desired position behind a subject. In this state, the subject is irradiated with radiation by driving the radiation source, and a radiographic image of the subject is acquired by detecting the radiation transmitted through the subject using the radiation detector.

The radiographic image acquired by the imaging of the subject is displayed on a monitor provided at the body part, and is confirmed by a user. Additionally, the monitor displays various kinds of information required for control of the radiation irradiation device, or receives input of various instructions required for operation of the radiation irradiation device in a case where the monitor is a monitor of a touch panel type.

SUMMARY OF THE INVENTION

Here, in the general portable radiation irradiation devices, the monitor is provided to be fixed to the body part. Thus, the position of the monitor cannot be changed.

However, in a case where the user stands behind the body part, depending on the position of installation of the monitor to the body part, a visual field in front of the user may be blocked, and may become an obstacle. Additionally, in a case where the monitor of the touch panel type is provided, there is also a case where input to the monitor may be easier in a case where the monitor is located at a position closer to a user's dominant arm than in a case where the monitor is located at a front position with respect to the user. Moreover, in a case where the user changes the position of a radiation source attached to the tip of the arm part or performs an input operation on an operating part provided at the radiation source, and in a case where the user moves from the rear of the body part to the front side, there is a case where the monitor provided on the body part may become an obstacle and may not easily move smoothly. Additionally, in a case where the user changes the position of the radiation source or in a case where the user is performing an input operation on the operating part, the user moves to the front side of the device. Thus, there is a case where it may be difficult to view the display of the monitor.

That is, in a case where the position of the monitor is fixed with respect to the body part, there is a case where the monitor may become an obstacle for a certain reason or it may be difficult to view the display of the monitor.

An object of the invention is to provide a radiation irradiation device enabling a user to change the position of a monitor to a desired position as needed and smoothly perform imaging of a radiographic image, in view of the above problems.

A radiation irradiation device of the invention comprises a radiation generation unit that generates radiation; an arm part having one end to which the radiation generation unit is attached; a body part to which the other end of the arm part is connected; a leg part that is provided on a bottom surface of the body part and is capable of traveling on a device placement surface; and a display unit provided on a surface that faces the bottom surface of the body part, via a connecting member. The display unit is detachably installed at a plurality of positions on the surface that faces the bottom surface of the body part.

Additionally, in the radiation irradiation device of the above invention, it is preferable that, in a case where a side toward which the arm part extends from the body part is defined as a front side during use of the device, the display unit is detachably installed at at least one of a left position or a right position with a connecting portion of the arm part to the body part as a center.

Additionally, in the radiation irradiation device of the invention, in a case where a side toward which the arm part extends from the body part is defined as a front side during the use of the device, a radiation source handle part or an operating part that receives an input operation may be provided on a left side or a right side of the radiation generation unit, and the display unit may be detachably installed at a position opposite to a side where the radiation source handle part or the operating part is provided.

Additionally, in the radiation irradiation device of the invention, the radiation source handle part or the operating part may be provided on the left side of the radiation generation unit, and wherein the display unit is detachably installed at a right position with the connecting portion of the arm part to the body part as a center.

Additionally, in the radiation irradiation device of the invention, in the case where the side toward which the arm part extends from the body part is defined as the front side during the use of the device, a radiation source handle part or an operating part that receives an input operation may be provided on a left side or a right side of the radiation generation unit, and the display unit may be detachably installed at a position on the same side as the side where the radiation source handle part or the operating part is provided.

Additionally, it is preferable that the radiation irradiation device of the above invention further comprises a body handle part provided vertically above the surface that faces the bottom surface of the body part, the connecting member is connected to the surface that faces the bottom surface of the body part at a position vertically below the body handle part, and the display unit is provided such that a vertically lower end part is located vertically above the body handle part.

Additionally, in the radiation irradiation device of the above invention, it is preferable that, in a case where a side toward which the arm part extends from the body part is defined as a front side during use of the device, the leg part has a front wheel and a rear wheel, and the display unit is detachably installed in front of an axle of the rear wheel.

Additionally, in the radiation irradiation device of the above invention, it is preferable that, in a case where a side toward which the arm part extends from the body part is defined as a front side during use of the device, the display unit is detachably installed behind a connecting portion of the arm part to the body part.

Additionally, in the radiation irradiation device of the above invention, the display unit may be connected to the connecting member so as to be rotationally movable.

Additionally, in the radiation irradiation device of the above invention, the display unit may be rotationally movable with at least two axes as central axes with respect to the connecting member.

Additionally, in the radiation irradiation device of the above invention, in the case where the side toward which the arm part extends from the body part is defined as the front side during use of the device, the display unit may be rotationally movable with an axis extending in a right and left direction as a central axis.

Additionally, in the radiation irradiation device of the above invention, the display unit is rotationally movable such that a display surface is parallel to a vertical direction and a horizontal direction.

Additionally, in the radiation irradiation device of the above invention, the display unit may be installed to be rotatable with an axis passing through a center of a connecting portion between the connecting member and the body part and extending in a vertical direction as a central axis.

Additionally, in the radiation irradiation device of the above invention, the display unit may include a wireless communication unit.

Additionally, in the radiation irradiation device of the above invention, the wireless communication unit may be detachable with respect to the display unit.

Additionally, in the radiation irradiation device of the above invention, a plurality of the wireless communication units are provided.

Additionally, the radiation irradiation device of the invention may further comprise a first wireless communication unit that performs wireless communication with a radiation detector that detects radiation radiated to a subject; and a second wireless communication unit that performs wireless communication with a local area network.

Additionally, the radiation irradiation device of the above invention may further comprise a wireless communication unit built in the display unit; and a wireless communication unit that is detachable with respect to the display unit.

According to the radiation irradiation device of the invention, the display unit can be detachably installed at the plurality of positions on the surface that faces the bottom surface of the body part. Thus, a user can change the position of the display unit to the desired position as needed. Accordingly, a radiographic image can be smoothly captured while viewing the display of the display unit, for example, without the display unit becoming an obstacle. Additionally, the monitor can be installed at a position where the user can see easily.

Additionally, in a case where the display unit is of a touch panel type, input to the display unit becomes easy by installing the display unit at a position closer to a user's dominant arm.

DESCRIPTION OF THE PREFERRED EMBODIMENTS

Figure 1:
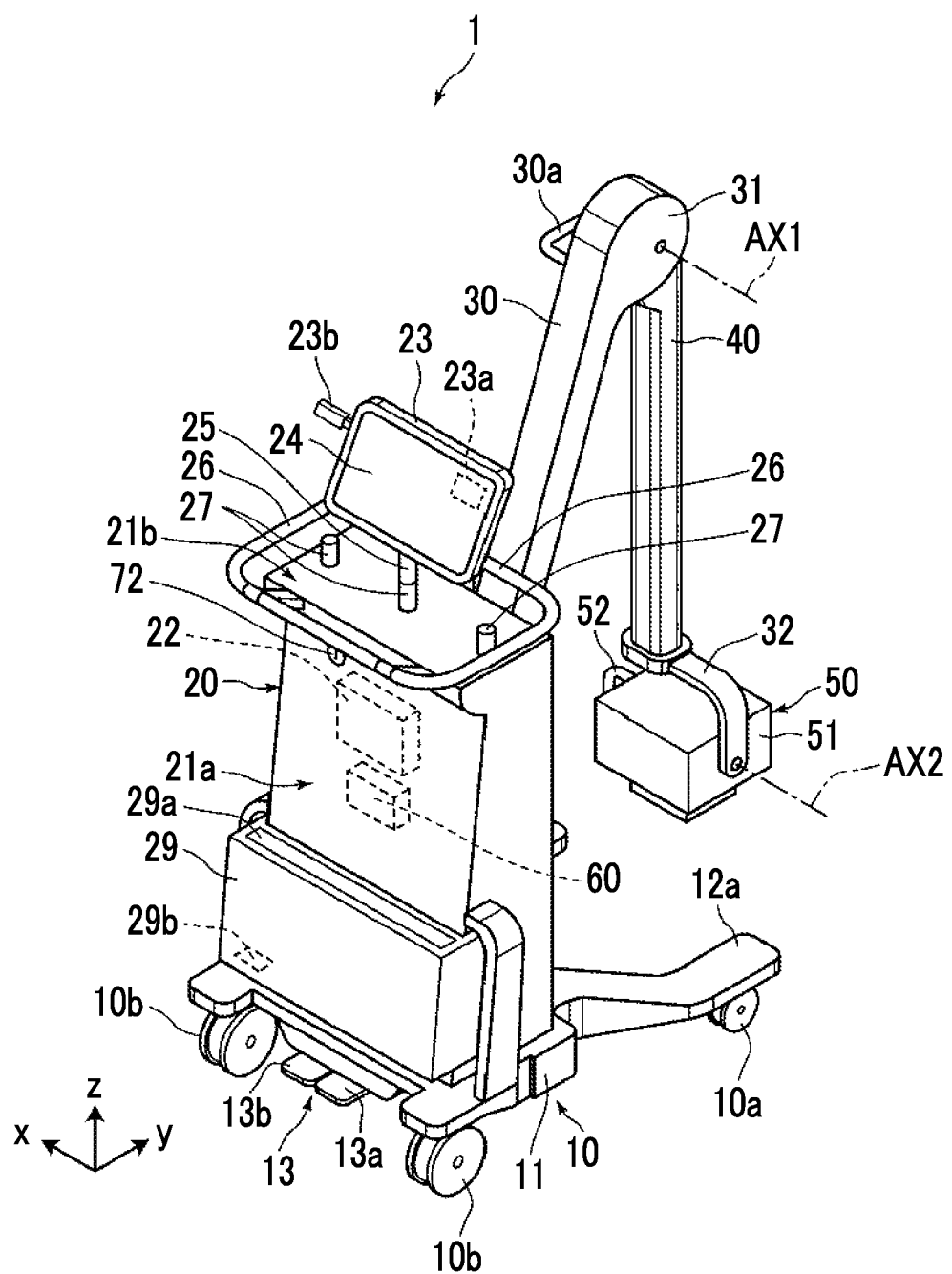
FIG. 1 is a perspective view illustrating an entire shape of a radiation irradiation device of an embodiment of the invention.
Figure 2:
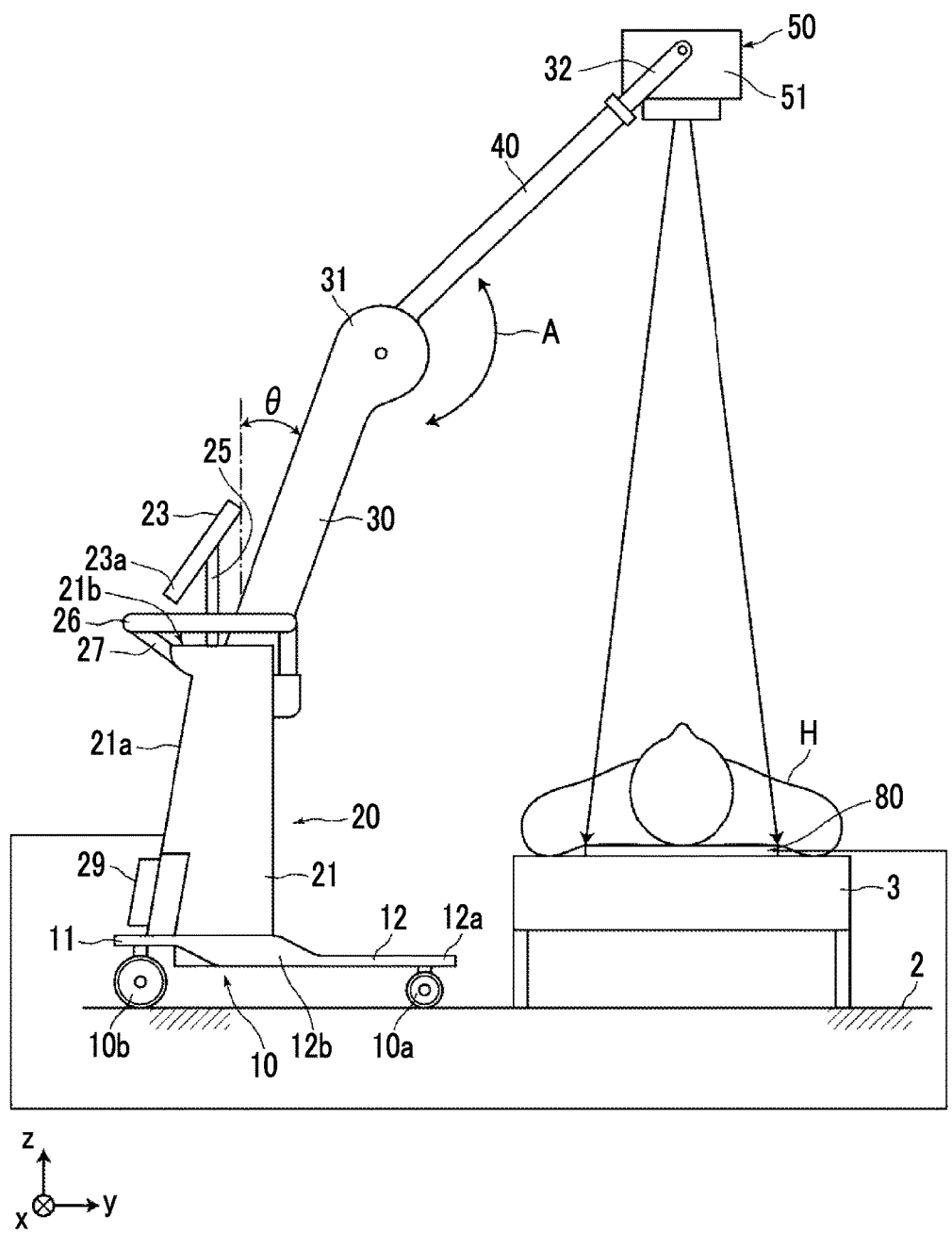
FIG. 2 is a view illustrating the state of the radiation irradiation device of the embodiment of the invention in a case where the device is used.

Hereinafter, a radiation irradiation device of an embodiment of the invention will be described in detail, referring to the drawings. FIG. 1 is a perspective view illustrating the entire shape of the radiation irradiation device of the present embodiment in a case where the device is not used, and FIG. 2 is a side view illustrating the state of the radiation irradiation device of the present embodiment in a case where the device is used. In addition, in the following, an upper side and a lower side in the vertical direction in a state where the radiation irradiation device is placed, for example, a device placement surface, such as a floor of a medical institution, are referred to as "up" and "down", respectively, and a direction perpendicular to the vertical direction in the same state is referred to as a "horizontal" direction. Additionally, in the views to be described below, the vertical direction is defined as a z direction, a right and left direction of the radiation irradiation device is defined as an x direction, and a forward-backward direction of the radiation irradiation device is defined as a y direction. In addition, the front herein means a side toward which an arm part is extended from a body part of the radiation irradiation device in a case where the device is used.

As illustrated in FIGS. 1 and 2, a radiation irradiation device 1 of the present embodiment includes a leg part 10, a body part 20, a first support part 30, a second support part 40, and a radiation generation unit 50. In addition, in the present embodiment, the arm part is constituted of the first support part 30 and the second support part 40.

Figure 3:
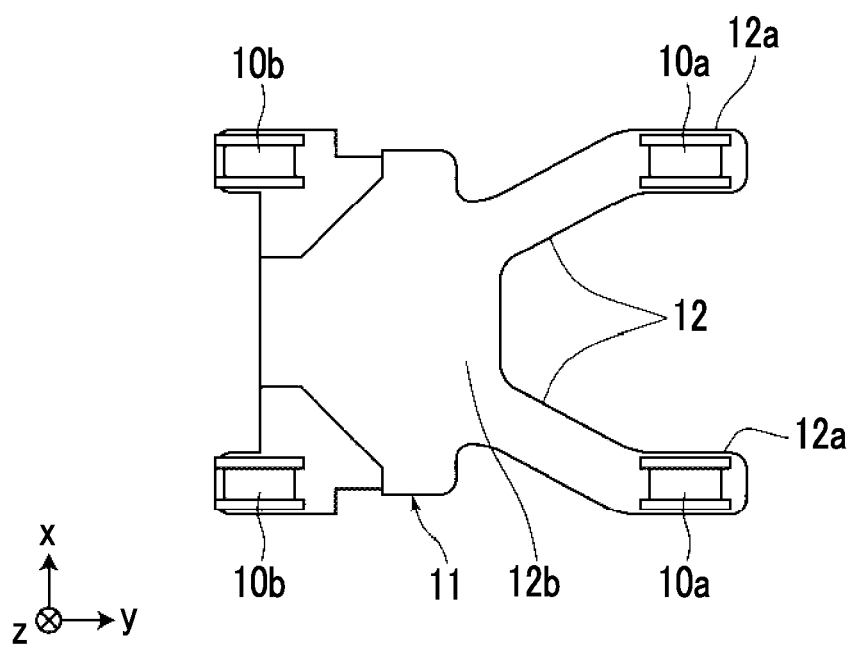
FIG. 3 is a view of a leg part as seen from below.

The leg part 10 is capable of traveling on a device placement surface 2, and includes a plate-shaped pedestal part 11 on which the body part 20 is placed, and a foot arm part 12 that extends from the pedestal part 11 toward the front. FIG. 3 is a view of the leg part 10 as seen from below. As illustrated in FIG. 3, the foot arm part 12 is formed in a V shape that widens in the right and left direction toward the front.

The leg part 10 includes first casters 10a and second casters 10b. The first casters 10a are respectively provided on bottom surfaces of two tip parts 12a at the front of the foot arm part 12, and second casters 10b are respectively provided on bottom surfaces of two corners at the rear of the pedestal part 11. By forming the foot arm part 12 in a V shape as described above, for example, as compared to a case where the entire leg part 10 is formed in a rectangular shape, an edge part of the leg part does not easily collide against its surrounding obstacle in a case where the leg part 10 is rotated. Thus, handling can be made easy. Additionally, weight reduction can also be achieved.

Additionally, as illustrated in FIG. 2, the foot arm part 12 is formed such that the thickness of the two front tip parts 12a in the vertical direction is smaller than the thickness of a V-shaped root part 12b in the vertical direction. In this way, by making the thickness of the two front tip parts 12a of the foot arm part 12 small, it is possible to make the two tip parts 12a easier to enter a location under a bed where a subject is sleeping, or the like, and it is possible to use the device in a narrower space. In addition, the V-shaped root part means a portion where the legs that widen in the right and left direction toward the front join together at the rear side.

Each first caster 10a has a shaft that extends in the upward-downward direction, and is attached to a bottom surface of the foot arm part 12 such that a rotating shaft of a wheel is revolvable within a horizontal plane about the shaft of the first caster. Additionally, each second caster 10b also has a shaft that extends in the upward-downward direction, and is attached to a bottom surface of the pedestal part 11 such that a rotating shaft of a wheel is revolvable within the horizontal plane about the shaft of the second caster. In addition, the rotating shaft of each wheel herein is a rotating shaft in a case where the wheel rotates and travels. The leg part 10 is configured so as to be capable of traveling in a certain direction on the device placement surface 2 by the first casters 10a and the second casters 10b.

Additionally, as illustrated in FIG. 1, a pedal part 13 is provided at the rear of the leg part 10. The pedal part 13 is constituted of two pedals of a first pedal 13a and a second pedal 13b. The first pedal 13a is a pedal for bringing the second casters 10b into a non-revolvable state. As a user steps on the first pedal 13a, the second casters 10b are configured so as to be locked in revolution by a locking mechanism and brought into the non-revolvable state.

Additionally, the second pedal 13b is a pedal for bringing the second casters 10b into a revolvable state from the non-revolvable state. As the user steps on the second pedal 13b, the second casters 10b are configured so as to be released from the locking by the locking mechanism and brought into the revolvable state again.

A well-known configuration can be used as the locking mechanism that locks the revolution of the second casters 10b. For example, the revolution may be locked such that both sides of the wheels of the second casters 10b are sandwiches by plate-shaped members, or the revolution may be locked by providing members that stop the rotation of shafts of the second casters 10b that extend in the upward-downward direction.

The body part 20 is placed on the pedestal part 11 of the leg part 10, and includes a housing 21. A control unit 22 that controls driving of the radiation irradiation device 1 and a charging part 60 are housed within the housing 21.

The control unit 22 performs control regarding generation of radiation and irradiation with radiation, such as a tube current, irradiation time, and a tube voltage, in the radiation generation unit 50, and control regarding acquisition of radiographic images, such as image processing of a radiographic image acquired by a radiation detector to be described below. The control unit 22 is configured of, for example, a computer in which a program for control is installed, exclusive hardware, or a combination of both.

The charging part 60 includes a battery, and charges the radiation detector held by a cradle 29 to be described below. In addition, the charging part 60 is connected to an external power source via a connector (not illustrated), and the battery is charged under the supply of electrical power from the external power source.

Additionally, a monitor 25 is attached to a surface 21b (hereinafter referred to as a monitor installation surface 21b) that faces a bottom surface of the body part 20 via a pillar-shaped connecting member 25. In the present embodiment, the monitor 23 is equivalent to a display unit.

The monitor 23 consists of a liquid crystal panel or the like, and displays a radiographic image acquired by imaging of a subject, and various kinds of information required for the control of the radiation irradiation device 1. Additionally, the monitor 23 includes a touch panel type input unit 24, and receives input of various instructions required for the operation of the radiation irradiation device 1. Specifically, input for setting of imaging conditions and input for imaging, that is, emission of radiation, is received. In addition, instead of the touch panel type input unit 24, buttons for performing various operations may be included as the input unit.

Additionally, a first wireless communication unit 23a is built in the monitor 23. The first wireless communication unit 23a performs wireless communication with the radiation detector to be described below. The first wireless communication unit 23a transmits a control signal output from the control unit 22 within the body part 20 toward a wireless communication unit of the radiation detector. Additionally, the first wireless communication unit 23a receives a radiographic image output from the wireless communication unit of the radiation detector, and outputs this image to the control unit 22. The control unit 22 displays the input radiographic image on the monitor 23.

Additionally, a second wireless communication unit 23b is attached to the monitor 23. The second wireless communication unit 23b is configured to be detachable with respect to a connector provided at the monitor 23. The second wireless communication unit 23b and the monitor 23 are connected to each other, for example, by a universal serial bus (USB) connector.

The second wireless communication unit 23b is capable of performing wireless communication with a local area network provided within a hospital or the like, and is capable of receiving various kinds of information from various devices installed within the hospital via the local area network. The information received by the second wireless communication unit 23b is acquired by the control unit 22, and is used for various control or is displayed on the monitor 23. Additionally, the second wireless communication unit 23b is capable of transmitting the information received by the input unit 24 of the monitor 23 to the devices installed within the hospital via the local area network.

In addition, in the present embodiment, the first wireless communication unit 23a that performs wireless communication with the radiation detector is built within the monitor 23, and the second wireless communication unit 23b that performs wireless communication with the local area network within the hospital is configured to be detachable with respect to the monitor 23. However, the invention is not limited to this. For example, contrary to this, the first wireless communication unit that performs wireless communication with the radiation detector may be detachably configured, and the second wireless communication unit that performs wireless communication with the local area network within the hospital may be built within the monitor 23. Additionally, both of the first wireless communication unit and the second wireless communication unit may be built within the monitor 23, or both of the first wireless communication unit and the second wireless communication unit may be configured to be detachable with respect to the monitor 23.

Additionally, the first wireless communication unit 23a and the second wireless communication unit 23b may also be used as access points, or may relay wireless communication between the devices installed within the hospital.

Additionally, a wireless communication unit, which performs wireless communication with the devices installed within the hospital, may be detachably configured in addition to the second wireless communication unit 23b.

Additionally, the first wireless communication unit 23a and the second wireless communication unit 23b do not have to be separate bodies, and may be configured as one wireless communication unit such that both the communication with the radiation detector and the communication with the local area network are performed by the one wireless communication unit.

Additionally, in the present embodiment, the control unit 22 is installed within the body part 20. However, the invention is not limited to this, and the control unit 22 may be provided inside the monitor 23. In this case, since a distance between the control unit 22, and the first wireless communication unit 23a and the second wireless communication unit 23b can be shortened, the noise in a signal between the control unit 22, and the first wireless communication unit 23a and the second wireless communication unit 23b can be reduced.

The monitor installation surface 21b is provided with a plurality of monitor installation parts 27 to which a connecting member 25 provided at the monitor 23 is configured to be detachable. Each monitor installation part 27 is configured such that the connecting member 25 is fitted thereinto, for example, is constituted of a tubular member into which the pillar-shaped connecting member 25 is inserted. In the present embodiment, the connecting member 25 is formed in a columnar shape, and the monitor installation part 27 is formed in a cylindrical shape. In a case where the connecting member 25 is fitted to the monitor installation part 27, the connecting member 25 is configured to be rotatable with an axis extending in a length direction thereof as a central axis. That is, by configuring the invention in this way, the monitor 23 is installed to be rotatable with an axis passing through the center of a connecting portion between the connecting member 25 and the body part 20 and extending in the vertical direction as a central axis.

An outer peripheral surface of the columnar connecting member 25 and an inner peripheral surface of the cylindrical monitor installation part 27 are in contact with each other with a certain degree of frictional coefficient, and is rotationally movable as a strong external force is applied thereto by the user, and does not rotate unless an external force is applied.

In addition, in the present embodiment, as described above, the monitor 23 is adapted to constitute the connecting member 25 and the monitor installation part 27 so as to be rotatable. However, the invention is not limited to this, the monitor 23 may be configured such that the monitor 23 does not rotate. Specifically, for example, the connecting member 25 may be formed in a prismatic shape, for example, and the monitor installation part 27 may be formed in a tubular shape adapted to the shape of the connecting member 25. Alternatively, in a case where, as in the present embodiment, the connecting member 25 is formed in a columnar shape and the monitor installation part 27 is formed in a cylindrical shape, a protrusion may be formed on the outer peripheral surface of the connecting member 25, a recess may be formed in the monitor installation part 27, and the connecting member 25 and the monitor installation part 27 may be configured to be non-rotatable by fitting the protrusion and the recess to each other.

As illustrated in FIG. 1, the plurality of monitor installation parts 27 are provided on the monitor installation surface 21b. Accordingly, the monitor 23 can be installed at a plurality of positions on the monitor installation surface 21b. In addition, as for a power source for the monitor 23, the monitor 23 may be provided with a chargeable battery and the battery may be charged by the external power source, or supply of electrical power may be received from the charging part 60 of the body part 20 in a case where the monitor 23 is connected to a monitor installation part 27.

In the present embodiment, the monitor installation parts 27 are provided at a left position and a right position with a connecting portion of the first support part 30 to the body part 20 as a center, and at a center position on a line passing through the above center and extending in the forward-backward direction. In addition, the arrangement of the monitor installation part 27 is not limited to this, and other arrangements may be adopted. For example, the monitor installation parts 27 may be provided at either the left position or the right position with the connecting portion of the first support part 30 to the body part 20 as a center, and at the above center position.

Additionally, as illustrated in FIG. 2, the monitor installation parts 27 are provided rearward of the connecting portion of the first support part 30 to the body part 20. Accordingly, the user can view the monitor 23 without being disturbed by the first support part 30, and the visibility of the monitor 23 can be improved.

Additionally, as illustrated in FIG. 2, the monitor installation parts 27 are provided forward of axles of the second casters 10b. Accordingly, since the relatively heavy monitor 23 can be installed forward of the axles of the second casters 10b, the gravity center position of the entire device can be brought closer to the front, and the device can be made it difficult to fall rearward.

Figure 4:
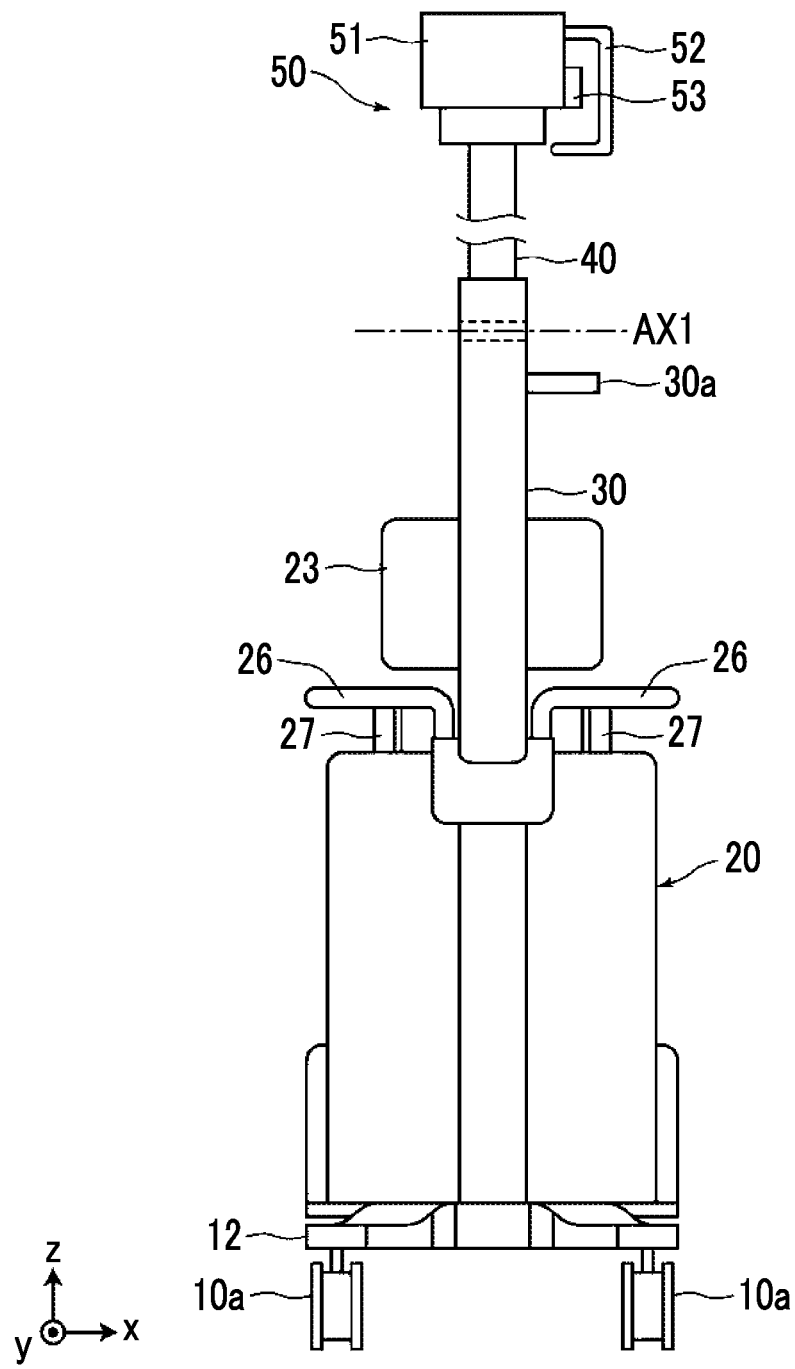
FIG. 4 is a view of the radiation irradiation device illustrated in FIG. 1 as seen from the front.
Figure 5:
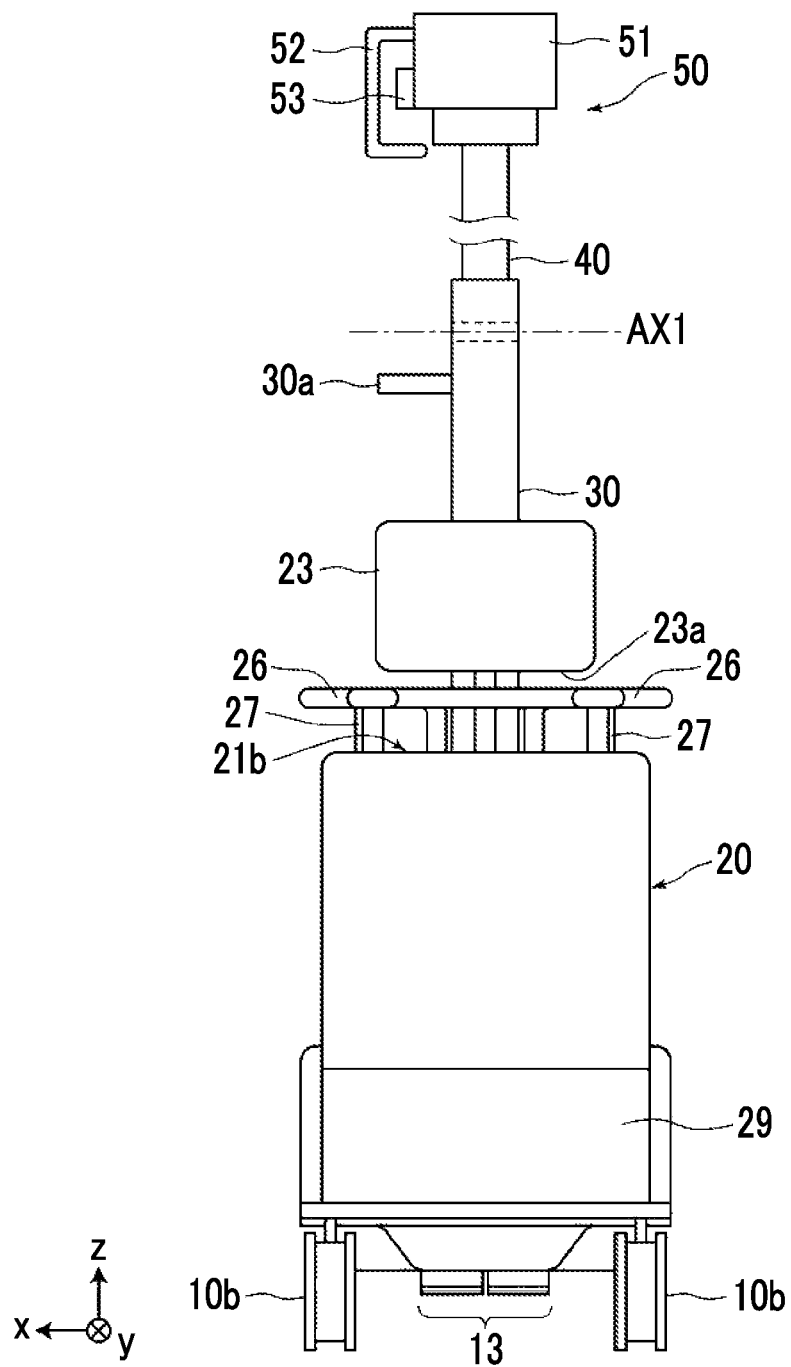
FIG. 5 is a view of the radiation irradiation device illustrated in FIG. 1 as seen from the rear.

Additionally, a body handle part 26 for pushing or pulling the radiation irradiation device 1 is attached to an upper side, in the vertical direction, of the monitor installation surface 21b of the body part 20. The body handle part 26 is provided so as to go around the housing 21, and is configured so as to be capable of being held not only from a rear side of the radiation irradiation device 1 but also from a front side or a lateral side. FIG. 4 is a view of the radiation irradiation device 1 as seen from the front. As illustrated in FIG. 4, the body handle part 26 is provided so as to go around to a front side of the body part 20. FIG. 5 is a view of the radiation irradiation device 1 as seen from the rear.

As illustrated in FIGS. 2 and 5, the connecting member 25 is connected to the monitor installation surface 21b on a lower side in the vertical direction with respect to the body handle part 26, and the monitor 23 is provided such that an end part 23a of the monitor 23 on the lower side in the vertical direction is located on an upper side in the vertical direction with respect to the body handle part 26. By configuring the invention in this way, the user can view the monitor 23 without being disturbed by the body handle part 26, and the visibility of the monitor 23 can be improved.

Additionally, the body part 20 is configured to be capable of housing the radiation detector on the surface thereof opposite to a side where the first support part 30 is attached. The radiation detector detects the radiation radiated onto the subject, and for example, a cassette type radiation detector including a housing is used as the radiation detector. Specifically, for example, a radiation detector including a scintillator (fluorescent body) that converts incident radiation into visible light, a photoelectric conversion layer that converts the visible light into electrical signals, and a thin film transistor (TFT) active matrix substrate. The radiation detector includes a wireless communication unit that performs wireless communication with the first wireless communication unit 23a built in the above-described monitor 23, and outputs a detected radiographic image to the first wireless communication unit 23a via wireless communication. Additionally, the wireless communication unit of the radiation detector receives the control signal output from the control unit 22 within the body part 20 and transmitted from the first wireless communication unit 23a. The operation of the radiation detector is controlled on the basis of the control signal received by the wireless communication unit.

As illustrated in FIGS. 1 and 2, the housing 21 of the body part 20 has a flat surface 21a inclined to the first support part 30 side, on a surface opposite to a side where the first support part 30 is attached, and the flat surface 21a is provided with the cradle 29.

An insertion port 29a for inserting the radiation detector is formed in an upper surface of the cradle 29. The insertion port 29a has an elongated shape of a size such that the radiation detector is fitted thereto. In the present embodiment, one end part of the radiation detector is inserted into the insertion port 29a, the one end part is supported by the cradle 29, and the radiation detector is held by the cradle 29. In this case, a front surface of the radiation detector is directed to the flat surface 21a side.

A connector 29b is attached to a bottom part of the cradle 29. The connector 29b is electrically connected to the connector of the radiation detector in a case where the radiation detector is held by the cradle 29. The connector 29b is electrically connected to the charging part 60. The charging part 60 charges the radiation detector via the connector 29b. In addition, the charging part 60 is connected to an external power source via a connector (not illustrated), and the battery is charged under the supply of electrical power from the external power source.

The radiation generation unit 50 is configured such that a radiation source, a collimator for narrowing the irradiation range of radiation, and the like is housed within a housing 51. The radiation source is constituted of, for example, an X-ray tube, a booster circuit, and cooling means for cooling the X-ray tube, and the like. Emission of the radiation from the radiation source of the radiation generation unit 50 is performed depending on an instruction from an input unit 24 in the monitor 23 by an operator.

Additionally, as illustrated in FIGS. 4 and 5, a radiation source handle part 52 and an operating part 53 are provided on a left side surface of the housing 51. The radiation source handle part 52 is formed in a U shape, and is configured so as to be capable of being held in a case where the user changes the position of the radiation generation unit 50. Additionally, the operating part 53 receives input operations for various kinds of setting, such as setting of a tube voltage and the like regarding the radiation source and setting of the restriction of the collimator.

Here, the above-described monitor installation parts 27 may not be necessarily provided on both the left side and the right side of the connecting portion between the first support part 30 and the body part 20 as in the present embodiment. However, it is desirable to provide the monitor installation parts 27 at least on a side opposite to a side where the radiation source handle part 52 and the operating part 53 are provided at the radiation generation unit 50. That is, in a case where the radiation source handle part 52 and the operating part 53 are provided on the left side of the radiation generation unit 50 as in the present embodiment, it is desirable that the monitor installation parts 27 are provided on the right side of the connecting portion between the first support part 30 and the body part 20.

By providing the monitor installation parts 27 in this way, the monitor 23 is located closer to the right in a case where the user goes around and moves from the rear side to the left side of the radiation irradiation device 1, holds the radiation source handle part 52, and changes the position of the radiation generation unit 50 or in a case where an input operation is performed on the operating part 53. Thus, the monitor 23 can be smoothly moved without becoming an obstacle. That is, in a case where the radiation source handle part 52 and the operating part 53 are provided on the right side of the radiation generation unit 50, it is desirable that the monitor installation parts 27 are provided on the left side of the connecting portion between the first support part 30 and the body part 20.

Additionally, from a viewpoint of the user's ease of movement, it is desirable to provide the monitor installation parts 27 as described above. However, from a viewpoint of the user's viewability of the monitor 23, it is desirable that the monitor installation parts 27 are provided at positions on the same side as a side where the radiation source handle part 52 and the operating part 53 are provided at the radiation generation unit 50. That is, in a case where the radiation source handle part 52 and the operating part 53 are provided on the left side of the radiation generation unit 50, for example, as in the present embodiment, and in a case where the monitor 23 is installed on the opposite side, there is also a viewpoint that it is difficult to see the display of the monitor 23 in a case where the user holds the radiation source handle part 52 to change the position of the radiation generation unit 50 or in a case where an input operation is performed on the operating part 53. Hence, from such a viewpoint, it is desirable that the monitor installation parts 27 are provided at the positions on the same side as the side where the radiation source handle part 52 and the operating part 53 are provided at the radiation generation unit 50.

Additionally, in the present embodiment, as described above, the first wireless communication unit 23a and the second wireless communication unit 23b are provided at the monitor 23. Thus, for example, in a case where the state of wireless communication is not good, the state of the wireless communication can be simply improved by changing the installation position of the monitor 23.

An L-shaped radiation source attachment part 32 is provided at a tip (one end) of the second support part 40. The radiation generation unit 50 is attached to the one end of the second support part 40 via the radiation source attachment part 32. The radiation generation unit 50 is connected to the radiation source attachment part 32 so as to be rotationally movable with an axis AX2 as a rotational movement axis. The rotational movement axis AX2 is an axis that extends in the right and left direction (x direction). In addition, the radiation source attachment part 32 holds the radiation generation unit 50 such that the radiation generation unit 50 moves rotationally via a friction mechanism. For this reason, the radiation generation unit 50 is rotationally movable by applying a certain degree of strong external force, and maintains a relative angle with respect to the second support part 40 without moving rotationally unless an external force is applied.

One end of the first support part 30 is connected to the other end of the second support part 40. The second support part 40 is connected to the first support part 30 so as to be rotationally movable with an axis AX1 as a rotational movement axis. The rotational movement axis AX1 is an axis that extends in the right and left direction (x direction). The second support part 40 moves rotationally in a direction of arrow A illustrated in FIG. 2 such that an angle formed with the first support part 30 is changed about the rotational movement axis AX1. That is, the second support part 40 moves rotationally only around one axis (the rotational movement axis AX1) that extends in the right and left direction. In the present embodiment, as described above, the orientation of the second support part 40 can be freely changed together with the body part 20 by the revolution of the first casters 10a and the second casters 10b. Thus, the degree of freedom of rotation of the second support part 40 can be lowered, and a simpler configuration can be adopted.

A rotational movement part 31 having the rotational movement axis AX1 holds the second support part 40 such that the second support part 40 moves rotationally via the friction mechanism. For this reason, the second support part 40 is rotationally movable by applying a certain degree of strong external force, and maintains a relative angle with respect to the first support part 30 without moving rotationally unless an external force is applied.

In addition, in the present embodiment, the second support part 40 does not have an extendable and retractable configuration, and is configured to be incapable of being extended and retracted. In the present embodiment, as described above, the orientation of the second support part 40 can be freely changed together with the body part 20 by the revolution of the first casters 10a and the second casters 10b. Thus, a configuration in which the second support part 40 is extended and retracted may not be provided, and a simpler configuration can be adopted. However, the invention is not limited to such a configuration and a configuration in which the second support part 40 is extendable and retractable may be adopted.

In addition, although the rotational movement of the second support part 40 and the radiation generation unit 50 is performed via the friction mechanism, rotational movement positions of these parts may be fixed by a well-known locking mechanism. In this case, the rotational movement of the second support part 40 and the radiation generation unit 50 becomes possible by releasing the locking mechanism. The rotational movement positions can be fixed by locking the locking mechanism at desired rotational movement positions.

The other end of the first support part 30 is connected to the surface of the body part 20 on the front side. The first support part 30 is provided so as to be fixed with respect to the body part 20, and is attached so as to be non-rotatable with respect to the body part 20. In the present embodiment, as described above, the orientation of the second support part 40 can be freely changed together with the body part 20 by the revolution of the first casters 10a and the second casters 10b. Thus, it is necessary to give the degree of freedom to the first support part 30, and a simpler configuration can be adopted. That is, the invention is not limited to such a configuration, and the first support part 30 may be configured so as to be rotatable with an axis passing through the center of the portion of the first support part 30 to the body part 20 and extending in the vertical direction as a rotational axis.

As illustrated in FIG. 2, the first support part 30 of the present embodiment is provided such that the inclination θ of the extension direction thereof with respect to the vertical direction become 10 degrees or more and 30 degrees or less. By setting the inclination θ of the first support part 30 to 10 degrees or more, the user's front visibility can be secured. Additionally, by setting the inclination θ of the first support part 30 to 30 degrees or less, the second support part 40 can be folded downward and the radiation generation unit 50 can be housed. Additionally, in a case where the radiation irradiation device 1 is used, a source image receptor distance (SID) can be secured.

In addition, the extension direction of the first support part 30 means an axial direction thereof in a case where the first support part 30 is formed linearly. Additionally, the extension direction means a direction in which a straight line connecting the center of each of both end parts of the first support part 30 extends in a case where the first support part 30 is formed in shapes, such as an arc, other than the straight line.

Additionally, a left side surface of the first support part 30 is provided with an arm handle part 30a. The arm handle part 30a is formed in an L shape, and is configured so as to be capable of being held in a case where the user changes the position of the radiation irradiation device 1.

Here, the above-described monitor installation parts 27 may not be necessarily provided on both the left side and the right side of the connecting portion between the first support part 30 and the body part 20 as in the present embodiment. However, it is desirable to provide the monitor installation parts 27 at least on a side opposite to a side where the arm handle part 30a of the first support part 30 is provided. That is, as in the present embodiment, in a case where the arm handle part 30a is provided on the left side of the first support part 30, it is desirable that the monitor installation parts 27 are provided on the right side of the connecting portion between the first support part 30 and the body part 20.

By providing the monitor installation parts 27 in this way, the monitor 23 is located closer to the right in a case where the user goes around and moves from the rear side to the left side of the radiation irradiation device 1, holds the arm handle part 30a, and changes the orientation of the radiation irradiation device 1. Thus, the monitor 23 can be smoothly moved without becoming an obstacle.

In the present embodiment, in a case where the subject is imaged, as illustrated in FIG. 2, the radiation detector 80 is disposed under the subject H that lies on ones' back on a bed 3. As the user rotationally moves the second support part 40 around the rotational movement axis AX1 in an illustrated counterclockwise direction from an initial position of the second support part 40 illustrated in FIG. 1, the radiation generation unit 50 is moved to a target position immediately above the subject H, as illustrated in FIG. 2.

The radiographic image of the subject H can be acquired by driving the radiation generation unit 50 according to an instruction from the input unit 24 to irradiate the subject H with radiation and detecting the radiation transmitted through the subject H, using the radiation detector 80, after the radiation generation unit 50 is moved to the target position. In addition, the radiation detector 80 and the radiation irradiation device 1 are connected together with or without wires. Accordingly, the radiographic image of the subject H acquired by the radiation detector 80 is directly input to the radiation irradiation device 1.

Figure 6:
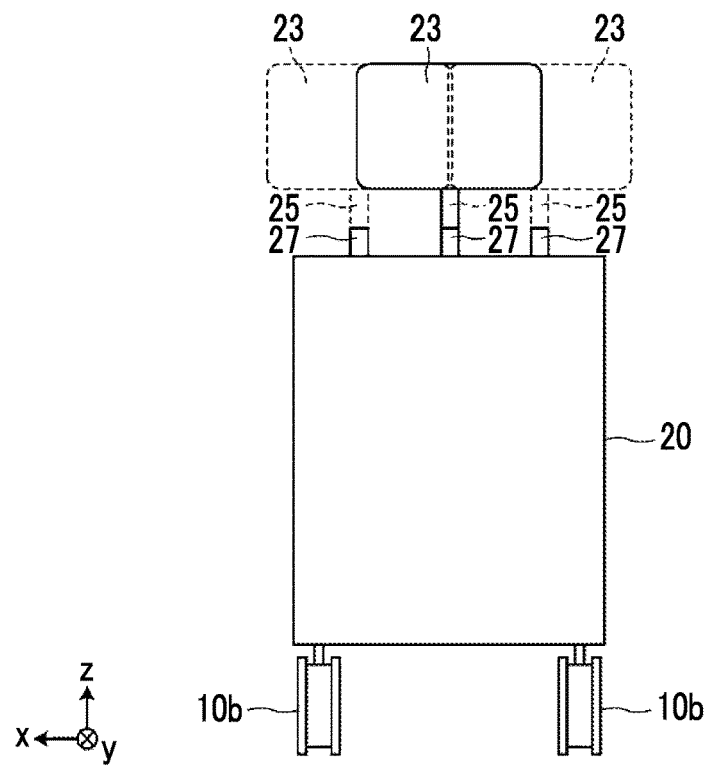
FIG. 6 is a view for explaining a change in an installation position of a monitor.

In the case of the imaging of the subject as described above, as illustrated in FIG. 6, the user can connect the connecting member 25 of the monitor 23 to a desired monitor installation part 27 as needed, and dispose the monitor 23 at a desired position. For example, setting input to the input unit 24 of the monitor 23 can be made easy by installing the monitor 23 on the right side in a case where the user is a right-handed person or by installing the monitor 23 on the left side in a case where the user is a left-handed person. Additionally, by installing the monitor 23 on the left side or the right side, the visual field of a front surface in a case where the user stands behind the radiation irradiation device 1 can be secured. In addition, in FIG. 6, illustration of components other than the body part 20, the second casters 10b, the monitor installation parts 27, the connecting member 25, and the monitor 23 is omitted, and the body part 20 is schematically illustrated.

Figure 7:
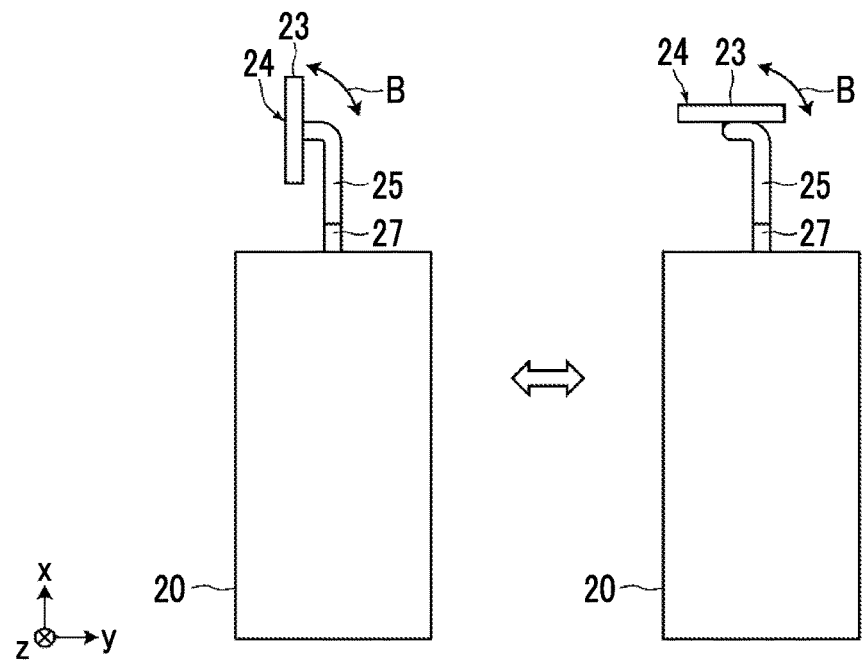
FIG. 7 is a view for explaining an example in which the monitor is configured so as to be rotationally movable.

Additionally in the radiation irradiation device 1 of the above embodiment, it is desirable to connect the monitor 23 to the connecting member 25 so as to be rotationally movable. Specifically, as illustrated in FIG. 7, it is desirable to make the monitor 23 rotationally movable with an axis extending in the right and left direction (x direction) as a rotational movement axis. In this case, it is desirable to make the monitor 23 rotationally movable such that the input unit 24 (equivalent to a display surface) of the monitor 23 is parallel to the vertical direction (the z direction) and the horizontal direction. In addition, in FIG. 7, illustration of components other than the body part 20, the monitor installation parts 27, the connecting member 25, and the monitor 23 is omitted, and the body part 20 is schematically illustrated.

By making the monitor 23 rotationally movable such that the input unit 24 of the monitor 23 is parallel to the horizontal direction, the visual field of the user's front surface can be secured, for example, in a case where the user stands behind the radiation irradiation device 1 and moves the radiation irradiation device 1. Additionally, the invention is not limited to the configured as above, and the monitor 23 may be configured to be rotationally movable with an axis extending in the forward-backward direction (y direction) as a rotational movement axis. By configuring the invention in this way, the input unit 24 of the monitor 23 can be directed to the user side in accordance with a position where the user stands with respect to the radiation irradiation device 1.

Figure 8:
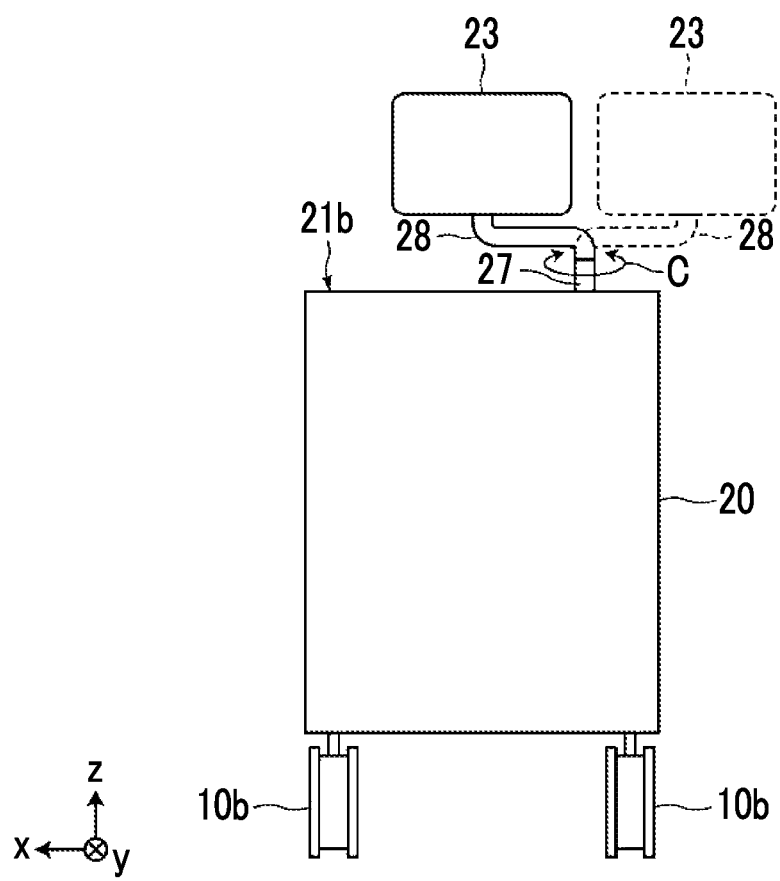
FIG. 8 is a view illustrating an example of a configuration in which the monitor is capable of being disposed outside a body part.

Additionally, as illustrated in FIG. 8, a connecting member 28 may be constituted of a member having a portion extending in the horizontal direction, and the connecting member 28 may be configured to be rotatable in a direction of arrow C with an axis passing through the center of a monitor installation part 27 and extending in the vertical direction as a central axis. By configuring the invention in this way, effective utilization of the device, such as such as putting things on the monitor installation surface 21b of the body part 20, can be made by rotating a portion extending in the horizontal direction of the connecting member 28 from the body part 20 side to the outside (a side illustrated by a dotted line in FIG. 8). It is desirable that the portion extending in the horizontal direction of the connecting member 28 has a length such that such that at least the range of half of the monitor 23 is disposed outside the body part. In addition, in FIG. 8, illustration of components other than the body part 20, the monitor installation parts 27, the connecting member 28, and the monitor 23 is omitted, and the body part 20 is schematically illustrated.

Figure 9:
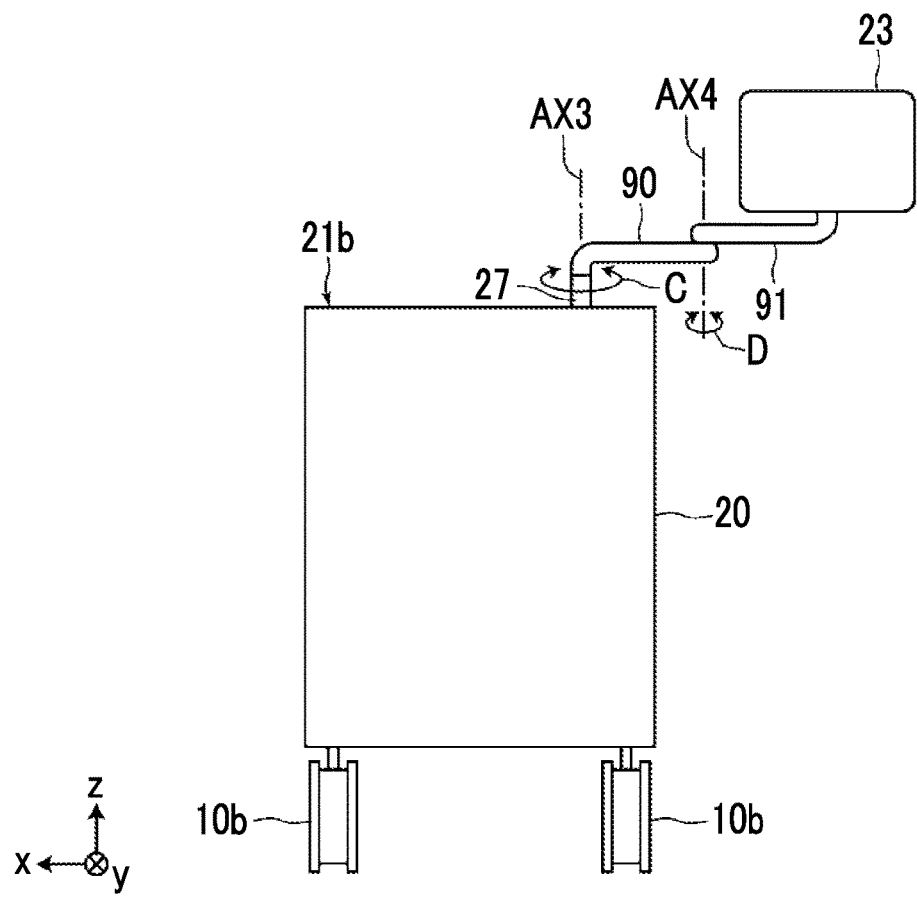
FIG. 9 is a view illustrating another configuration of a connecting portion between the monitor and the body part.

Additionally, as illustrated in FIG. 9, the monitor 23 may be configured to be capable of being connected to a monitor installation part 27 via a first connecting member 90 and a second connecting member 91. The first connecting member 90 is configured to be rotatable in the direction of arrow C, with an axis AX3 passing through the center of the monitor installation part 27 and extending in the vertical direction as a central axis, similarly to the connecting member 28 illustrated in FIG. 8. Additionally, the second connecting member 91 has one end connected to the monitor 23 and has the other end connected to the first connecting member 90. The second connecting member 91 is configured to be rotatable in a direction of arrow D in a connecting portion connected to the first connecting member 90. That is, the second connecting member 91 is configured to be rotatable in the direction of arrow D with an axis AX4 passing through the center of the connecting portion connected to the first connecting member 90 and extending in the vertical direction as a central axis. By configuring the invention in this way, the degree of freedom of the installation position of the monitor 23 can be further increased. In addition, the monitor 23 may be configured to be rotatable in a connecting portion connected to the second connecting member 91. Also in FIG. 9, illustration of components other than the body part 20, the monitor installation parts 27, first connecting member 90, second connecting member 91, and the monitor 23 is omitted, and the body part 20 is schematically illustrated.

In addition, in the radiation irradiation device 1 of an above embodiment, the radiation source handle part 52 is provided only on the left side of the radiation generation unit 50. However, the radiation source handle part 52 may be provided on both the left and right sides.

EXPLANATION OF REFERENCES

1: radiation irradiation device
10: leg part
10a: first caster
10b: second caster
11: pedestal part
12: foot arm part
13: pedal part
20: body part
21b: monitor installation surface
22: control unit
23: monitor
23a: first wireless communication unit
23b: second wireless communication unit
24: input unit
25: connecting member
26: body handle part
27: monitor installation part
28: connecting member
30: first support part
30a arm handle part
31: rotational movement part
32: radiation source attachment part
40: second support part
50: radiation generation unit
51: housing
52: radiation source handle part
53: operating part
80: radiation detector
90: first connecting member 91: second connecting member

What is claimed is:

1. A radiation irradiation device comprising:
a radiation generation unit that generates radiation;
an arm part having one end to which the radiation generation unit is attached;
a body part to which the other end of the arm part is connected;
a leg part that is provided on a bottom surface of the body part and is capable of traveling on a device placement surface;
a display unit provided on a surface that faces the bottom surface of the body part, via a connecting member; and
a plurality of monitor installation parts provided on the surface that faces the bottom surface of the body part,
wherein the display unit is detachably and attachably installed at one of the monitor installation parts via the connecting member.

2. The radiation irradiation device according to claim 1, wherein in a case where a side toward which the arm part extends from the body part is defined as a front side during use of the device, the display unit is detachably and attachably installed at at least one of a left position or a right position with a connecting portion of the arm part to the body part as a center.

3. The radiation irradiation device according to claim 2, wherein in a case where a side toward which the arm part extends from the body part is defined as a front side during the use of the device, a radiation source handle part or an operating part that receives an input operation is provided on a left side or a right side of the radiation generation unit, and
wherein the display unit is detachably and attachably installed at a position opposite to a side where the radiation source handle part or the operating part is provided.

4. The radiation irradiation device according to claim 3, wherein the radiation source handle part or the operating part is provided on the left side of the radiation generation unit, and
wherein the display unit is detachably and attachably installed at a right position with the connecting portion of the arm part to the body part as a center.

5. The radiation irradiation device according to claim 3, further comprising:
a body handle part provided vertically above the surface that faces the bottom surface of the body part,
wherein the connecting member is connected to the surface that faces the bottom surface of the body part at a position vertically below the body handle part, and the display unit is provided such that a vertically lower end part of the display unit is located vertically above the body handle part.

6. The radiation irradiation device according to claim 2, wherein in a case where a side toward which the arm part extends from the body part is defined as a front side during the use of the device, a radiation source handle part or an operating part that receives an input operation is provided on a left side or a right side of the radiation generation unit, and
wherein the display unit is detachably and attachably installed at a position on the same side as the side where the radiation source handle part or the operating part is provided.

7. The radiation irradiation device according to claim 2, further comprising:
a body handle part provided vertically above the surface that faces the bottom surface of the body part,
wherein the connecting member is connected to the surface that faces the bottom surface of the body part at a position vertically below the body handle part, and the display unit is provided such that a vertically lower end part of the display unit is located vertically above the body handle part.

8. The radiation irradiation device according to claim 1, further comprising:
a body handle part provided vertically above the surface that faces the bottom surface of the body part,
wherein the connecting member is connected to the surface that faces the bottom surface of the body part at a position vertically below the body handle part, and the display unit is provided such that a vertically lower end part of the display unit is located vertically above the body handle part.

9. The radiation irradiation device according to claim 8, wherein the body handle part encircles the monitor installation parts.

10. The radiation irradiation device according to claim 1, wherein in a case where a side toward which the arm part extends from the body part is defined as a front side during use of the device, the leg part has a front wheel and a rear wheel, and
wherein the display unit is detachably and attachably installed in front of an axle of the rear wheel.

11. The radiation irradiation device according to claim 1, wherein in a case where a side toward which the arm part extends from the body part is defined as a front side during use of the device, the display unit is detachably and attachably installed behind a connecting portion of the arm part to the body part.

12. The radiation irradiation device according to claim 1, wherein the display unit is connected to the connecting member so as to be rotationally movable.

13. The radiation irradiation device according to claim 12, wherein the display unit is rotationally movable with at least two axes as central axes with respect to the connecting member.

14. The radiation irradiation device according to claim 13, wherein in a case where a side toward which the arm part extends from the body part is defined as a front side during use of the device, the display unit is rotationally movable with an axis extending in a right and left direction as a central axis.

15. The radiation irradiation device according to claim 13, wherein the display unit is rotationally movable such that a display surface is parallel to a vertical direction and a horizontal direction.

16. The radiation irradiation device according to claim 1, wherein the display unit is installed to be rotatable with an axis passing through a center of a connecting portion between the connecting member and the body part and extending in a vertical direction as a central axis.

17. The radiation irradiation device according to claim 1, wherein the display unit includes a wireless communication unit.

18. The radiation irradiation device according to claim 17, wherein the wireless communication unit is detachable and attachable with respect to the display unit.

19. The radiation irradiation device according to claim 17, wherein a plurality of the wireless communication units are provided.

20. The radiation irradiation device according to claim 19, further comprising:

a first wireless communication unit that performs wireless communication with a radiation detector that detects radiation radiated to a subject; and a second wireless communication unit that performs wireless communication with a local area network.

21. The radiation irradiation device according to claim 19, further comprising:

a wireless communication unit built in the display unit; and a wireless communication unit that is detachable and attachable with respect to the display unit.

* * * * *